United States Patent
Cook et al.

[11] Patent Number: 6,159,006
[45] Date of Patent: Dec. 12, 2000

[54] PORTABLE ORAL IRRIGATOR

[75] Inventors: Stuart A. Cook, Duluth, Ga.; Michael Bigler, Bern, Switzerland

[73] Assignee: Conair Corporation, Stamford, Conn.

[21] Appl. No.: 09/226,877

[22] Filed: Jan. 6, 1999

[51] Int. Cl.[7] .................................................. A61H 7/00
[52] U.S. Cl. ................................................ 433/80; 601/165
[58] Field of Search ................................... 601/162–165, 601/160; 433/80

[56] References Cited

U.S. PATENT DOCUMENTS

| | | | |
|---|---|---|---|
| 3,703,170 | 11/1972 | Ruckman, Jr. | 601/162 |
| 3,771,517 | 11/1973 | Radecki | 601/165 |
| 4,236,889 | 12/1980 | Wright | 601/162 |
| 4,452,238 | 6/1984 | Kerr | 601/162 |
| 4,808,109 | 2/1989 | Thornton | 601/165 |
| 5,086,756 | 2/1992 | Powell | 601/165 |
| 5,142,723 | 9/1992 | Lustig et al. | 601/165 |

*Primary Examiner*—Ralph A. Lewis
*Attorney, Agent, or Firm*—Ohlandt, Greeley, Ruggiero & Perle, L.L.P.

[57] ABSTRACT

The present invention discloses a portable oral irrigator that is made up of a housing, a pump within the housing, a tube adapted to bring liquid to the pump, and an outlet for discharging a pulsating stream of liquid from the pump. The outlet includes a tip adapted for insertion into an oral cavity, and the tube has a first end and a second end, the first end being attached to the housing and the second end being free, thus enabling the second end to be placed by a user in a container of liquid.

21 Claims, 5 Drawing Sheets

PORTABLE ORAL IRRIGATOR

FIELD OF THE INVENTION

The present invention relates to a portable oral irrigation device used to flush the teeth and gums of plaque and debris. More particularly, it relates to a portable oral irrigation device having a fluid inlet tube with a free end, and a pump to expel streams of fluid from the device.

BACKGROUND OF THE INVENTION

Oral irrigation devices have achieved consumer acceptance as an integral element of regular dental hygiene. The pulsating jets of water or other fluids generated by these devices serve to stimulate gums, flush debris from interdental crevices, power away plague and tartar, and generally freshen the teeth, gums, tongue, tonsils a d other oral surfaces. The primary limitation of these devices has been their substantial size, necessitated by the incorporation of an integral fluid reservoir. The reservoir must be large enough to accommodate sufficient fluid for a typical use, without requiring the user to turn off the device, lay the handpiece down, and refill the reservoir. This large reservoir has required the known oral irrigation devices to be rather bulky. This has discouraged many users who find it difficult to store the device in, for example, a bathroom. Moreover, users find it difficult or impossible to take the large device with them when traveling.

Thus, a need exists for an oral irrigation device that is more compact, and more portable, than those now available. Similarly, a need exists for an oral irrigation device that has a water reservoir that is easily cleaned, easily refilled, and easily replaced if necessary. The present invention achieves these goals.

SUMMARY OF THE INVENTION

The present invention is a portable oral irrigator that is made up of a housing, a pump within the housing, a tube adapted to bring liquid to the pump, and an outlet for discharging a pulsating stream of liquid from the pump. The outlet includes a tip adapted for insertion into an oral cavity. The tube has a first end and a second end, the first end being attached to the housing and the second end being free, enabling it to be placed by a user in a container of liquid. In this portable oral irrigator, the housing preferably includes a base member and a removable head, and the pump and the tube are associated with the removable head. In addition, the tube can include a clip or other affixing means for affixing the tube to the container of liquid.

The pump is preferably a reciprocating pump in which pumping motion is generated through a rotating ramped cam. In addition, it is preferred that the housing have a bottom surface that is flat, and that the portable oral irrigator be balanced to enable the portable oral irrigator to stand upright on a flat surface. The first end of the tube can be detachable from the housing to facilitate cleaning. The liquid preferably includes water. The tip is preferably an angled tip. Also, the tube includes both a substantially flexible portion and a substantially inflexible portion, where the substantially inflexible portion is adapted for insertion into a container of fluid.

A method of irrigating an oral cavity is also disclosed that includes the steps of: filling a container at least partially with a fluid; inserting a free end of a tube into the container, where the tube is affixed to a portable oral irrigator, and the portable oral irrigator includes a pump and a tip adapted for insertion into the oral cavity; directing the tip at the oral cavity; and activating the pump of the portable oral irrigator to generate a stream of fluid into the oral cavity.

The fluid preferably includes water, and the container is preferably a cup, bottle, can, bag or sink. The tube can be removably affixed to the container. Moreover, the free end of the tube can be inserted into the container before the container is filled at least partially with fluid. Furthermore, when the portable oral irrigator 30 includes a power base and a detachable head portion, and the tube and the pump are located on the detachable head portion, the method can further include the step of detaching the detachable head portion from the power base to enable another detachable head portion to be attached to the power base. The stream generated is preferably pulsating.

In addition, a portable oral irrigator is disclosed that includes a power source; a motor adapted to be powered by the power source; a drive shaft adapted to be rotated by the motor; a pump adapted to be powered by the drive shaft, the pump including an inlet aperture, a fluid chamber, an outlet chamber and a piston that alternately seals off the inlet aperture and the outlet aperture as it rotates. The piston further includes a bearing and a ramped cam to convert rotational motion to reciprocating linear motion, such that the piston reciprocates to form a vacuum within the fluid chamber when the piston has sealed off the outlet aperture, and expels a jet of fluid from the fluid chamber when the piston has sealed off the inlet aperture.

DESCRIPTION OF THE PREFERRED EMBODIMENTS

The portable oral irrigators of the present invention preferably include an inlet tube that has a free end, thus adapting the device for use with any available container of water, such as a cup or a sink. The device also includes a rotating cam that provides a reciprocating pump action capable of generating high force pulsing jets of water. Thus, this oral irrigation device is much more easily transported than known devices having built-in fluid reservoirs. In addition, it takes up less space, and thus is more acceptable to consumers, even when portability is not a priority.

Figure 1:
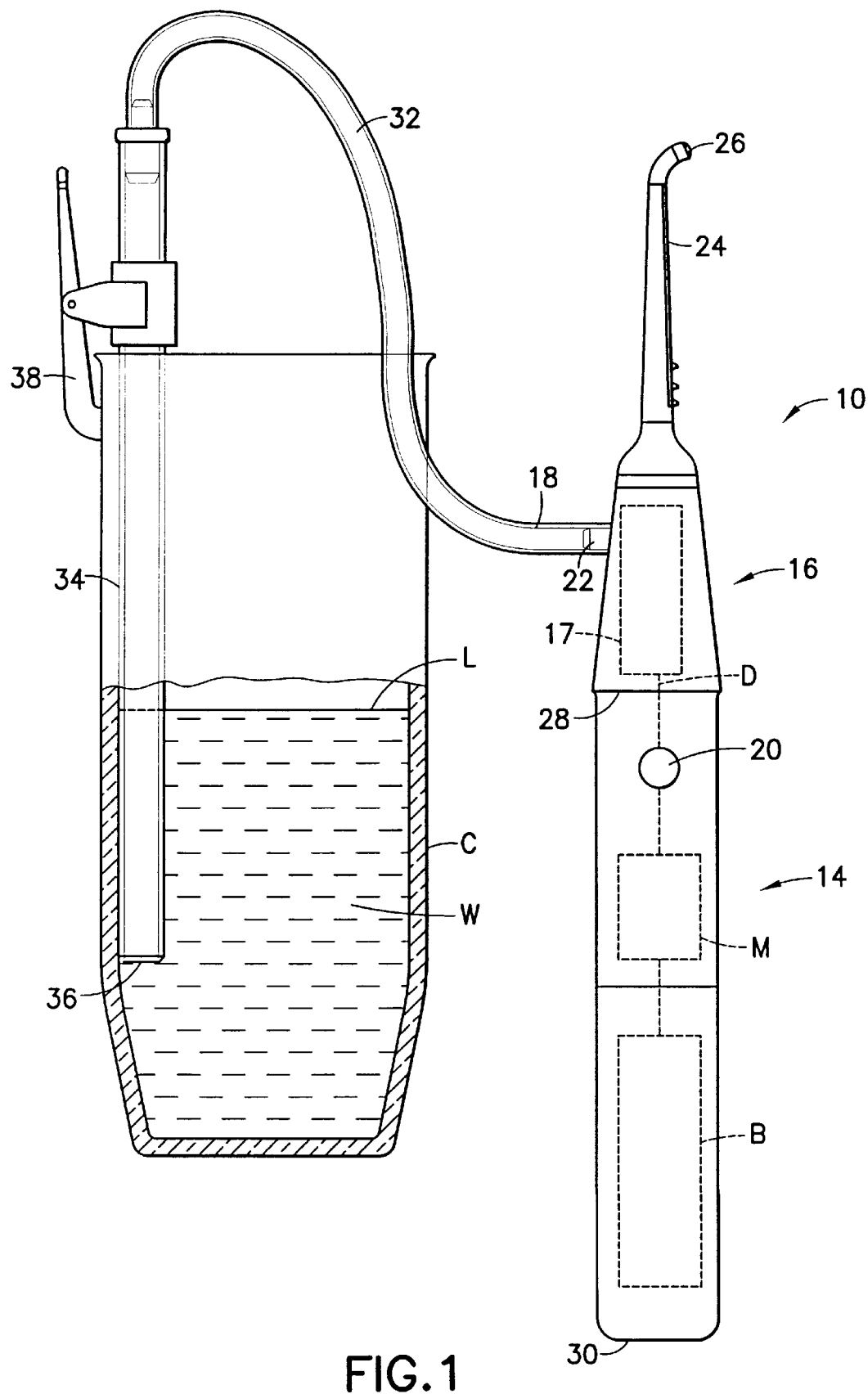
FIG. 1 is a perspective view of a preferred oral irrigator incorporating the invention, affixed to a cup of water.

An oral irrigation device according to a preferred embodiment of the present invention is shown in FIG. 1. The oral irrigator 10 includes power base 14, detachable head 16, and inlet tube 18. Inlet tube~18 is shown inserted in cup C containing water W. Located on power base 14 is on/off button 20, which activates and deactivates oral irrigator 10 when pressed by the user.

Figure 2:
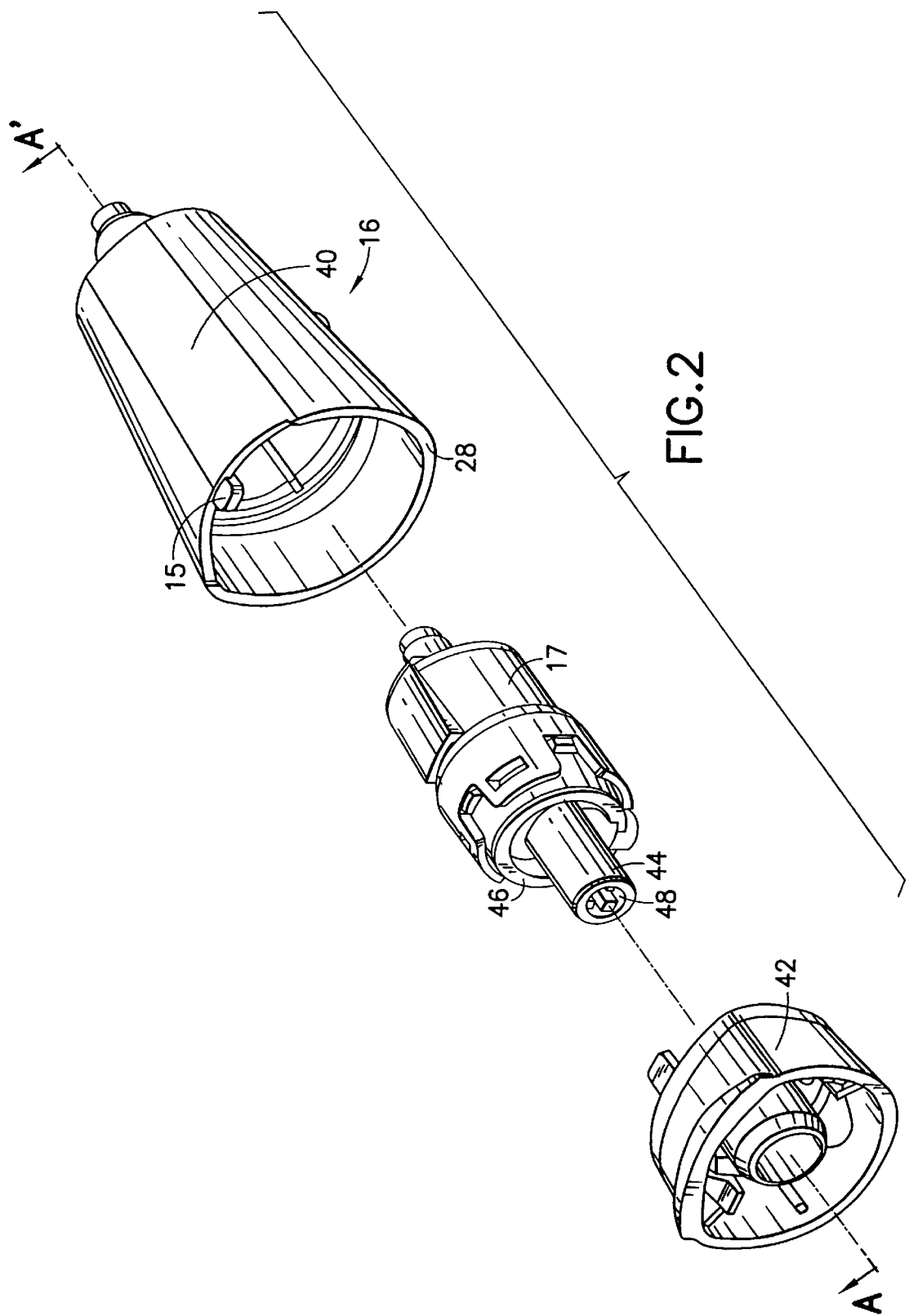
FIG. 2 is an exploded perspective view of components of the pump assembly of the oral irrigator of FIG. 1.
Figure 3:
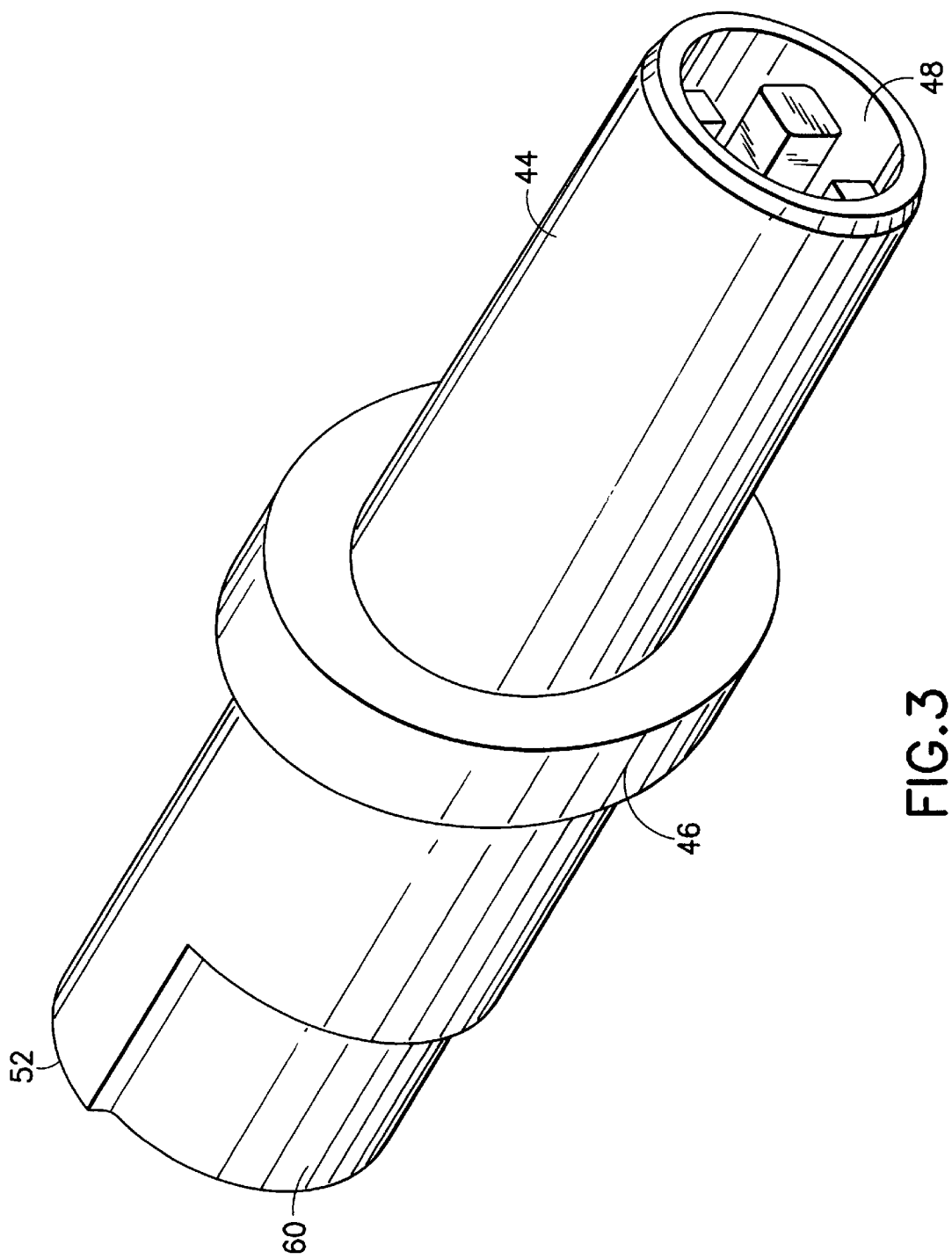
FIG. 3 is a perspective view of the cam of the pump assembly of FIG. 2.

In this preferred embodiment, oral irrigator 25 includes a detachable head 16 and a power base 14. Head 16 preferably engages power base 14 via snap-lock tabs 15 (see FIG. 2)

that are conventional in the art. The head 16 is easily released from power base 14, enabling other attachments such as an electric toothbrush or gum massager to be attached to, and powered by, power base 14. Power base 14 preferably includes a rechargeable battery source B (shown diagrammatically in phantom) that can be recharged by placing the power base 14 in a separate recharging stand. However, power base 14 can also include replaceable, disposable batteries.

If properly insulated to prevent electric shock, power base 14 can also derive energy through a standard electric plug. Alternatively, power base 14 and head 16 can be a single, permanently attached unit. Power base 14 also includes a motor M connected to battery source B (shown diagrammatically in phantom) and capable of driving the attachment, preferably head 16.

In the preferred embodiment, head 16 includes pump 17 (shown diagrammatically in FIG. 1, and in greater detail in FIGS. 2 through 4B). Motor M and pump 17 are linked by drive shaft D, which conveys motion (preferably rotational) from motor M to pump 17. Because in this preferred embodiment, power base 14 and head 16 are detachable, drive shaft B must also be separable from motor M or pump 17, or must be made up of two separable elements.

In the preferred embodiment of FIG. 1, head 16 includes tube coupling 22, adapted to engage an end of inlet tube 18. Detachable head 16 also includes a curved spray tip 24 having an outlet 26 from which the water or other fluid is jetted during use. The head 16 preferably includes a substantially flat (although not solid) lower surface 28, and is appropriately balanced to stand upright on a countertop or other surface. Similarly, power base 14 preferably has a flat lower surface 30. When affixed to head 16, the oral irrigator 10 is also preferably balanced to stand upright on a countertop or other surface. In this embodiment, inlet tube 18 is affixed to tube coupling 22 on head 16, preferably by means of a friction fit. Inlet tube 18 is preferably formed of a flexible and somewhat deformable material that can be pushed onto and over tube coupling 22 to form a water tight seal.

Inlet tube 18 is also preferably detachable from tube coupling 22 to allow the user to replace or clean the parts, as needed. More preferably, inlet tube 18 is formed of two primary portions, namely a substantially flexible portion 32 and a substantially inflexible portion 34. Flexible portion 32 of inlet tube 18 is easily flexed into different configurations, thus enabling inlet tube 18 to reach a cup C easily, regardless of its height or position.

Flexible portion 32 of inlet tube 18 preferably is connected to inflexible portion 34 of inlet tube 18 by a friction fit Inflexible portion 34 of inlet tube 18 is designed for easy insertion into cup C. Its relative rigidity keeps its free end 36 in position to allow an unobstructed flow of fluid from cup C and enables the user to know that the free end 36 is below the water level L. Alternatively, oral irrigator 10 can be adapted for use with a disposable straw-type inlet tube 18, preferably a bendable straw. Inlet tube 18 is preferably translucent or clear in whole or in part, to permit the user to view the fluid passing through it, and to ensure that inlet tube 18 is not blocked and is clear of debris or dirt.

Inlet tube 18 preferably includes a movable clip 38 or other attachment means for holding inlet tube 18 in position in cup C, and at a distance above the bottom of the cup C. If free end 36 of inlet tube 18 rests on the bottom of cup C, the fluid flow therethrough can be compromised unless the bottom of tube 18 is scalloped to allow fluid ingress. Clip 38 is preferably affixed to inflexible portion 34 of inlet tube 18, and is preferably adjustable along the length of inflexible portion 34 of inlet tube 18 or along the entire length of inlet tube 18, to permit it to attach to the lip or other amenable surface of cup C.

Cup C is a preferred fluid container for use in conjunction with the oral irrigator 10 of the present invention. Cup C shall encompass glasses, mugs, paper cups, bowls, storage tubs and all other conventional household beverage and liquid containers, for purposes of this invention. Alternatively, a sink can be used as the fluid container herein. Any fluid reservoir can be used herein, including plastic or foil bags/pouches and other non-rigid containers. Moreover, conventional bottles or cans of water, such as spring water, can also be used. This is optimal for use when traveling to locations without potable or safe tap water.

According to a preferred method of using oral irrigator 10, the user fills cup C with water W. Inlet tube 18, preferably already affixed to head 16, is moved close to cup C, and free end 36 of inlet tube 18 is placed in cup C well below water level L, but above the bottom of cup C. Inlet tube 18 is stabilized relative to cup C by means of clip 38. The user then actuates on/off button 20, powering motor M by means of battery source B. Motor M rotates drive shaft D, which drives pump 17. As further elaborated below, pump 17 draws water from cup C through inlet tube 18 into head IC, and sends the water through spray tip 24 and outlet 26, which the user has previously directed at the area to be irrigated. The streams or jets of water forced through outlet 26 provide the desired irrigation effect to teeth gums, tongue, etc.

Flexible portion 32 of inlet tube 18 is preferably long enough to allow the user a full range of motion in using oral irrigator 10 without pulling on or spilling cup C. The user can replenish the water supply during use by adding more water to cup C, if desired, or the user can simply re-actuate on/off button 20 to stop the irrigation session.

Further illustration of a preferred structure and function of pump 17 is provided in FIGS. 2 through 4B. Pump 17 preferably includes three main portions, namely casing 40, seat 42 and piston 44. Piston 44 is encased between casing 40 and seat 42. Of prime importance is ramped cam 46 (see FIGS. 3, 4A and 4B), which converts the rotating motion of drive shaft D to reciprocating linear pump action. Pump 17 further includes an inlet aperture 54, an outlet aperture 56, and a chamber 58. Inlet aperture 54 is associated with inlet tube 18, and outlet aperture 56 is associated with spray tip 24 and outlet 26. Piston 44 includes a keyed channel 48 adapted for engagement with drive shaft D by means of ears 49 (see FIG. 4B).

When drive shaft D is rotated by motor M, it rotates piston 44 and ramped cam 46. Ramped cam 46 rides on bearing 50 inside pump 17, thus causing top 52 of piston 44 to reciprocate between a lowest position in which top 52 is brought adjacent or close to inlet aperture 54, and a highest position in which top 52 minimizes the size of chamber 58. In addition, piston 44 includes a cutout 60 that extends about approximately one-half of the circumference of the top of piston 44. This cutout 60 is matched to the slope of ramped cam 46 such that when ramped cam 46 is in a lowermost position after a downstroke (see FIG. 4A), inlet aperture 54 is open to chamber 58 by means ofutout 60, allowing water to be drawn in (shown by arrows in FIG. 4A) and filling cutout 60 and chamber 58, at least partially. At this position, outlet aperture 56 is closed off by the full circumference of the opposite side of piston 44.

Figure 4A:
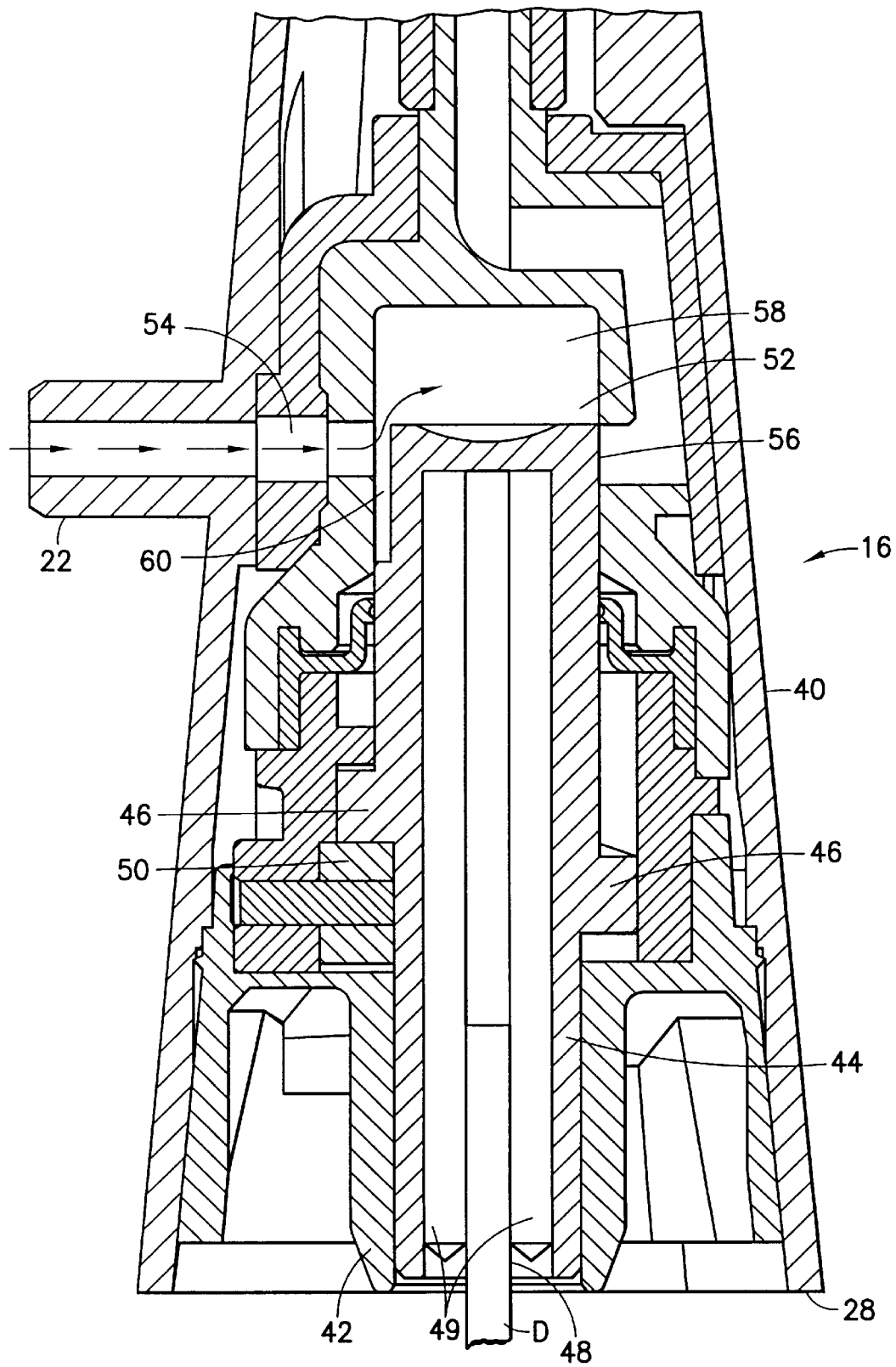
FIG. 4A is a cross-sectional diagram of the 30 assembled pump assembly of FIG. 2 along line A–A' in the direction indicated, shown in a first, water intake position.
Figure 4B:
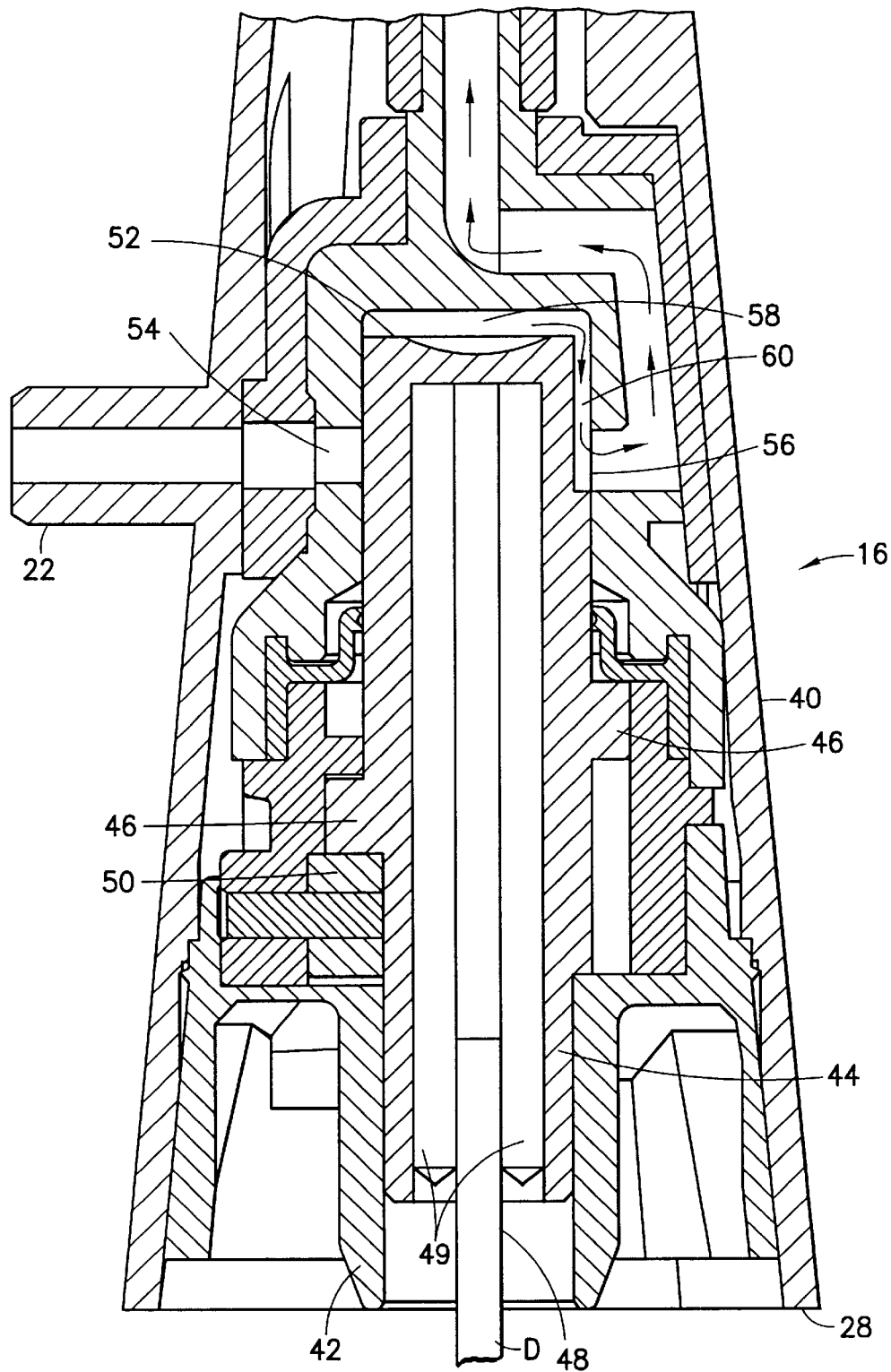
FIG. 4B is a cross-sectional diagram of the assembled pump assembly of FIG. 4A, shown in a second, water expulsion position.

As piston 44 continues to rotate, it rises up within chamber 58, and the full circumference of piston 44 rotates into engagement with inlet aperture 541 thus sealing it off from additional water intake (see FIG. 4A). The water that has entered chamber 58 is subjected to pressure by the rising top 52 of piston 44, and is expelled through cutout 60, which has now rotated into engagement with outlet aperture 56.

Thus, the water (depicted by arrows in FIG. 4B) is jetted under pressure through the narrow channel formed by cutout 60, further increasing the velocity of the water. Thus, a pulsed jet of water is produced that flows up spray tip 24 to outlet 26 and is expelled.

As ramped cam 46 continues to rotate, outlet aperture 56 is resealed, and inlet aperture 54 is reopened (FIG. 4A), allowing the cycle to repeat itself. Moreover, the rapid enlargement of chamber 58 caused by the drop of the top 52 of piston 44 causes a vacuum to form within chamber 58. This vacuum serves to draw water or other fluid through inlet aperture 54 25 (preferably from cup C through inlet tube 18) into chamber 58, thus generating the necessary vacuum pump action. This cycle generates repeated pulses or sprays of water from outlet 26.

Thus, ramped cam 46 converts the rotational movement of the drive shaft D into linear, reciprocating motion and vacuum sufficient to pump water through pump 47. This pumping mechanism is both efficient and compact, thus permitting oral irrigator 10 to be easily portable and easily handled, but without sacrificing irrigation performance.

The invention having been thus described with particular reference to the preferred forms thereof, it will be obvious that various changes and modifications may be made therein without departing from the spirit and scope of the invention as defined in the appended claims.

What is claimed is:

1. A portable oral irrigator comprising
   a housing;
   a power driven pump within said housing;
   a tube adapted to bring liquid to said pump; and
   an outlet for discharging a pulsating stream of liquid from said pump, said outlet having a tip adapted for insertion into an oral cavity,
   wherein said tube has a first end and a second end, said first end being attached to said housing, and said second end being free thus enabling said second end to be placed by a user in a container of liquid.

2. The portable oral irrigator of claim 1, wherein said housing includes a base member and a removable head disposed between said outlet and said tip.

3. The portable oral irrigator of claim 1, wherein said tube includes affixing means for affixing said tube to the container of liquid.

4. The portable oral irrigator of claim 3, wherein said affixing means includes a clip.

5. The portable oral irrigator of claim 1, wherein said pump is a reciprocating pump.

6. The portable oral irrigator of claim 5, wherein said reciprocating pump is connected to a ramped cam on a drive shaft rotated by said motor, and wherein said ramped cam converts rotation of said drive shaft to a linear motion.

7. The portable oral irrigator of claim 1, wherein said housing has a bottom surface that is flat.

8. The portable oral irrigator of claim 1, wherein said portable oral irrigator is balanced to enable said portable oral irrigator to stand upright on a flat surface.

9. The portable oral irrigator of claim 1, wherein said first end of said tube is detachable from said housing to facilitate cleaning.

10. The portable oral irrigator of claim 1, wherein said pulsating stream of liquid is a pulsating stream of water.

11. The portable oral irrigator of claim 1, wherein said tip is angled with respect to said outlet to form an angled tip.

12. The portable oral irrigator of claim 1, wherein said tube includes a substantially flexible portion and a substantially inflexible portion.

13. The portable oral irrigator of claim 12, wherein the substantially inflexible portion is adapted for insertion in the container of fluid.

14. A portable oral irrigation attachment adapted for engagement with a power base, said portable oral irrigation attachment comprising:
    a housing;
    a power driven pump within said housing;
    a tube adapted to bring liquid to said pump; and
    an outlet for discharging a stream of pulsating liquid from said pump, said outlet including a tip adapted for insertion into an oral cavity,
    wherein said tube has a first end and a second end, said first end being attached to said housing, and said second end being free thus enabling said second end to be placed by a user into a container of liquid.

15. A method of irrigating an oral cavity, comprising:
    filling a container at least partially with a fluid;
    inserting a free end of a tube into said container, said tube affixed to a portable oral irrigator, said portable oral irrigator including a power driven pump and a tip adapted for insertion into the oral cavity;
    directing said tip at the oral cavity; and
    activating said pump of said portable oral irrigator to generate a stream of fluid into the oral cavity.

16. The method of claim 15, wherein said fluid includes water.

17. The method of claim 15, wherein said container is selected from the group consisting of a cup, a bottle, a can, a bag and a sink.

18. The method of claim 15, further comprising the step of removably affixing said tube to said container.

19. The method of claim 15, wherein said portable oral irrigator includes a power base and a detachable head portion, and said tube and said pump are located on said detachable head portion, and further comprising the step of:
    detaching said detachable head portion from said power base to enable another detachable head portion to be attached to said power base.

20. The method of claim 15, wherein said stream of fluid is pulsating.

21. A portable oral irrigator comprising:
    a power source;
    a motor coupled to said power source;
    a drive shaft coupled to and rotated by said motor; and
    a pump including an inlet aperture, a fluid chamber, an outlet chamber and a piston coupled to and rotated by said drive shaft;
    said piston further includes a bearing and a ramped cam to convert rotational motion of said drive shaft to reciprocating linear motion of said piston, such that said piston alternately seals off said inlet aperture and said outlet aperture as it rotates and such that said piston reciprocates to form a vacuum within said fluid chamber when said piston has sealed off said outlet aperture drawing fluid into said fluid chamber through said inlet aperture and to form a pressure within said fluid chamber to jet fluid from said fluid chamber through said outlet aperture when said piston has sealed off said inlet aperture.

* * * * *